US009772278B2

(12) United States Patent
Han

(10) Patent No.: US 9,772,278 B2
(45) Date of Patent: Sep. 26, 2017

(54) MULTI-CHANNEL AEROSOL SCATTERING ABSORPTION MEASURING INSTRUMENT

(71) Applicant: Nanjing University, Nanjing, Jiangsu (CN)

(72) Inventor: Yong Han, Jiangsu (CN)

(73) Assignee: Nanjing University, Nanjing, Jiangsu (CN)

( * ) Notice: Subject to any disclaimer, the term of this patent is extended or adjusted under 35 U.S.C. 154(b) by 239 days.

(21) Appl. No.: 14/760,984

(22) PCT Filed: Jun. 26, 2014

(86) PCT No.: PCT/CN2014/080854
§ 371 (c)(1),
(2) Date: Jul. 14, 2015

(87) PCT Pub. No.: WO2015/180227
PCT Pub. Date: Dec. 3, 2015

(65) Prior Publication Data
US 2016/0274024 A1 Sep. 22, 2016

(30) Foreign Application Priority Data
May 28, 2014 (CN) .......................... 2014 1 0232392

(51) Int. Cl.
*G01N 21/39* (2006.01)
*G01N 21/49* (2006.01)
(Continued)

(52) U.S. Cl.
CPC ............... *G01N 21/39* (2013.01); *G01N 1/22* (2013.01); *G01N 21/1702* (2013.01);
(Continued)

(58) Field of Classification Search
CPC .......... G01N 1/22; G01N 21/49; G01N 15/02; G01N 2001/2223; G01N 2015/0046;
(Continued)

(56) References Cited

U.S. PATENT DOCUMENTS 5,793,478 A 8/1998 Rader et al.
5,933,245 A * 8/1999 Wood ................. G01N 21/1702
356/246

(Continued)

FOREIGN PATENT DOCUMENTS

CN 1368633 9/2002
CN 1654945 8/2005
(Continued)

OTHER PUBLICATIONS

Han et al.: "Measurement and analysis of extinction characteristics atmospheric visibility and aerosol based on scattering statistical", Infrared and Laser Engineering, Aug. 2008, vol. 37, No. 4, pp. 663-666 (w/ English Abstract).
(Continued)

*Primary Examiner* — Michael A Lyons
*Assistant Examiner* — Violeta A Prieto
(74) *Attorney, Agent, or Firm* — Rankin, Hill & Clark LLP

(57) ABSTRACT

The present invention discloses a multi-channel aerosol scattering absorption measuring instrument, comprising a light path device, a detection device and a gas path device. The light path device supplies three different wavelengths of laser entering the detection device in sequence; the detection device is provided with photoelectric detectors at multiple angles for measurement, so as to reduce the measurement error of aerosol scattering coefficient; the gas path device comprises a sample loading unit, a calibration unit and a sample discharging unit; and a light source from the light (Continued)

US 9,772,278 B2
Page 2 path device and a gas flow from the gas path device enter the photoacoustic cavity of the detection device respectively and are detected by a control unit. The aerosol scattering absorption measuring instrument of the present invention is characterized by multi-channel, multi-angular, full-scale and direct measurement of scattering phase function and absorption coefficient of aerosol particles, combines the function of synchronously acquiring the optical parameters of an aerosol (such as scattering coefficient, extinction coefficient, visibility, transmittance, single scattering albedo, etc.), and achieves the integrated on-line detection of different optical parameters of an aerosol with high automation degree and good stability.

10 Claims, 7 Drawing Sheets

(51) Int. Cl.
G01N 1/22 (2006.01)
G01N 21/17 (2006.01)
G01N 29/24 (2006.01)
G01N 21/53 (2006.01)
G01N 15/00 (2006.01)
G01N 23/227 (2006.01)
G01N 15/02 (2006.01)
G01N 21/03 (2006.01)
G01N 21/47 (2006.01)
G01N 21/05 (2006.01)

(52) U.S. Cl.
CPC ............ G01N 21/49 (2013.01); G01N 21/53 (2013.01); G01N 29/2425 (2013.01); G01N 15/02 (2013.01); G01N 21/0332 (2013.01); G01N 21/4785 (2013.01); G01N 23/227 (2013.01); G01N 2001/2223 (2013.01); G01N 2015/0046 (2013.01); G01N 2021/052 (2013.01); G01N 2021/1704 (2013.01); G01N 2021/4711 (2013.01); G01N 2201/06113 (2013.01)

(58) Field of Classification Search
CPC ........... G01N 2021/1704; G01N 21/53; G01N 29/2425; G01F 1/76; G10K 11/16
See application file for complete search history.

(56) References Cited

U.S. PATENT DOCUMENTS

| | | | | |
|---|---|---|---|---|
| 6,363,772 B1* | 4/2002 | Berry | ................. | G01N 21/1702 250/339.13 |
| 6,594,016 B1* | 7/2003 | Te Lintel Hekkert | ............. | G01N 21/1702 356/437 |
| 7,345,766 B2* | 3/2008 | Schindler | ........... | G01N 21/1702 356/437 |
| 2005/0160800 A1* | 7/2005 | Schindler | ........... | G01N 21/1702 73/61.71 |
| 2006/0290944 A1* | 12/2006 | Arnott | ................ | G01N 21/1702 356/519 |
| 2012/0055232 A1* | 3/2012 | Thorson | ............. | G01N 21/1702 73/24.02 |
| 2012/0279280 A1* | 11/2012 | Rezachek | .......... | G01N 21/1702 73/24.02 |

FOREIGN PATENT DOCUMENTS

| | | |
|---|---|---|
| CN | 2786619 | 6/2006 |
| CN | 101173886 | 5/2008 |

OTHER PUBLICATIONS

Moosmüller, H., Chakrabarty, R. K., and Arnott, W. P.: "Aerosol Light Absorption and its Measurement: A Review", J. Quant. Spectrosc. Radiat. Transfer, 2009. 110:844-878.

Zoltán Bozóki, Andrea Pogány & Gábor Szabó: "Photoacoustic Instruments for Practical Applications: Present, Potentials, and Future Challenges", Applied Spectroscopy Reviews, 2011,46:1, 1-37.

Lack, Daniel A., Lovejoy, Edward R., Baynard, Tahllee, Pettersson, Anders and Ravishankara, A. R.: "Aerosol Absorption Measurement using Photoacoustic Spectroscopy: Sensitivity, Calibration, and Uncertainty Developments", Aerosol Science and Technology, 2006, 40: 9, 697-708.

Tibor Ajtai, Ágnes Filep, Martin Schnaiter, Claudia Linke, Marlen Vragel, Zolta'n Bozo'ki, Ga'bor Szabo', Thomas Leisner, "A novelmulti-wavelength photoacoustic spectrometer for the measurement of the UV—vis-NIR spectral absorption coefficient of atmospheric aerosols", Journal of Aerosol Science 41 (2010) 1020-1029.

Liu Qiang, Huang Honghua, Wang Yao, Wang Guishi, Cao Zhensong, Liu Kun, Chen Weidong, Gao Xiaoming: "Multi-wavelength measurements of aerosol optical absorption coefficients using a photoacoustic spectrometer", Chinese Physics, 2014, vol. 23, No. 6, pp. 228-233.

Arnott, W. P., Hamasha, K., Moosmüller, H., Sheridan, P. J., and Ogren, J. A.: "Towards Aerosol Light-Absorption Measurements with a 7-Wavelength Aethalometer: Evaluation with a Photoacoustic Instrument and 3-Wavelength Nephelometer", Aerosol Sci. Tech. 2005, 39:17-29.

Haisch C., P. Menzenbach, H. Bladt, and R. Niessner, A Wide Spectral Range Photoacoustic Aerosol Absorption, Spectrometer, Analytical Chemistry, 2012, 84, 8941-8945.

Han Yong, Daren Lü, Ruizhong Rao, and Yingjian Wang: Determination of the complex refractive indices of aerosol from aerodynamic particle size spectrometer and integrating nephelometer measurements. Applied Optics, Jul. 20, 2009, vol. 48, No. 21, pp. 4108-4117.

T. Muller, M. Laborde, G. Kassell, and A. Wiedensohler: "Design and performance of a three-wavelength LED-based total scatter and backscatter integrating nephelometer", Atmos. Meas. Tech., 4, 1291-1303, 2011.

* cited by examiner

MULTI-CHANNEL AEROSOL SCATTERING ABSORPTION MEASURING INSTRUMENT

TECHNICAL FIELD

The present invention relates to an atmospheric aerosol absorption coefficient measuring apparatus, and in particular to a multi-channel aerosol scattering absorption measuring instrument.

BACKGROUND ART

Atmospheric aerosol is a mixture system composed of gases and particles having a certain stability and sedimentation velocity in the gravity field, also is a liquid or solid particulate system suspended in the atmosphere with a diameter of 0.001-100 μm, which is one of complex and harmful pollutants in the atmosphere environment. In terms of atmosphere energy balance, aerosols take effect on radiation transmission within a very wide range from ultraviolet, visible to infrared wavebands. The aerosphere layer where aerosols exist is heated under the optical effect of aerosols, so that the solar radiation reaching the ground surface is reduced to affect ground evaporation and water cycle as well, which is named as the direct effect of aerosols. Also, aerosols have the action of cloud condensation nuclei, a large amount of aerosol particles may cause the increase of number density of cloud droplets and leads to the decrease of mean radius of cloud droplets and reduction of rainfall and cloud amount, so that the radiation characteristics of cloud are changed, which is named as the indirect effect of aerosols. Because of the foregoing, the energy balance of ground-atmosphere system is changed, so that the conditions of climatic environment required for the survival of human beings are affected. Therefore, the researches about the direct and indirect effects of aerosols become the basic issue in atmosphere science.

At present, in the atmospheric sounding field in China, the routine observation of optical parameters of aerosols (such as scattering phase function and light absorption) has not been reported, the scientific observation at academic level of scattering and absorption characteristics of aerosols is still in progress, the synchronous and integrated measurement of all optical characteristics of aerosols (aerosol scattering coefficient, absorption coefficient, scattering phase function, extinction coefficient, transmittance, visibility and single scattering albedo) has not succeed, and there is a lack of scientific instruments for direct measurement of aerosol scattering phase function and single scattering albedo of aerosols. During the measurement of scattering coefficient and absorption coefficient of an aerosol through the known cavity ring-down spectroscopy, the aerosol absorption coefficient is determined by measuring the extinction coefficient and scattering coefficient. This method is indirect for the measurement of aerosol absorption coefficient, and fails to provide the direct measurement result of aerosol scattering phase function. Also, the presently-used scattering coefficient measurement lacks of the direct measurement result of light scattering intensity at paraxial narrow angle (e.g. integral turbidity measurement), which results in the large error of aerosol scattering coefficient measurement because of the lack of paraxial forward/backward scattering measurement.

SUMMARY OF THE INVENTION

An object of the present invention is to overcome the abovementioned problems in the prior art, provide a multi-channel aerosol scattering absorption measuring instrument which can synchronously acquiring scattering coefficient and absorption coefficient of multi-channel aerosols in different environments, and achieve the real-time on-line integrated measurement of aerosol optical parameters (such as scattering phase function, extinction coefficient, visibility, transmittance, single scattering albedo, etc.) with high automation degree and good stability.

In order to achieve the abovementioned object, the present invention is adopted to provide a multi-channel aerosol scattering absorption measuring instrument, which comprises a light path device, a detection device and a gas path device. Said light path device is used for supplying a light source. Said detection device comprises a control unit and a detection unit. Said detection unit comprises a photoacoustic cavity, a first long-range multiple reflector, a second long-range multiple reflector, six photoelectric detectors, a temperature/pressure/humidity sensor and a sound converter, wherein said first long-range multiple reflector and second long-range multiple reflector are positioned at the two ends of the photoacoustic cavity respectively, the first long-range multiple reflector (71) and second long-range multiple reflector (61) have the same reflection principle as Herriott optical long-range cells, the reflection results in a hollow cylindrical pillar formed by the light path between the two long-range multiple reflectors, so that a cavity is formed between the two long-range multiple reflectors, said photoacoustic cavity covers said two long-range multiple reflectors to form a detection cavity, one of said photoelectric detectors is arranged outside the detection device for measuring light intensity of the light source emitted from the detection unit, other photoelectric detectors are arranged on the surface of the photoacoustic cavity for measuring the scattering intensities of aerosols at different angles, said temperature/pressure/humidity sensor and sound converter are arranged on the inner surface of the photoacoustic cavity respectively, said sound converter is arranged in the middle position of the photoacoustic cavity and perpendicular to the long axis of the photoacoustic cavity, and said photoelectric detectors, temperature/pressure/humidity sensor and sound converter are connected to said control unit respectively. Said gas path device comprises a sample loading unit, a calibration unit and a sample discharging unit, wherein said sample loading unit and sample discharging unit communicate with the two ends of said photoacoustic cavity respectively, the light source from the light path device and a gas flow from the gas path device enter the photoacoustic cavity of the detection device and are detected by the control unit respectively. The detection principle of the photoacoustic cavity is that when the aerosol particles are exposed to the light, the particles absorb light energy to produce sound pressure and light-sound interconversion. As the value of sound pressure resulting from light energy absorption of a sample is measured by photoacoustic spectrometry, the interference of reflected light and scattered light on the measurement is reduced. The first long-range multiple reflector and second first long-range multiple reflector are implanted into the photoacoustic cavity, so as to greatly enhance detection signals of the sound converter and also make the measurement of transmittance easier. The sound converter (i.e. a microphone) is a detection sensor for direct measurement of aerosol absorption coefficient. Where, said temperature/pressure/humidity sensor is a sensor integrating the function of measuring temperature, pressure and humidity, and this temperature/pressure/humidity sensor can also be replaced by a temperature sensor, pressure sensor or humidity sensor working alone.

Preferably, said light path device comprises a laser transmission unit and a laser modulation unit, which are connected in sequence, said laser transmission unit comprises a laser and a controller of the laser, said laser transmission unit transmits a laser beam of 1064 nm fundamental wavelength, said laser modulation unit comprises a frequency multiplication unit, a frequency division unit and a light coupling unit, and said laser modulation unit modulates the fundamental laser beam of 1064 nm into laser beams of 1064 nm, 532 nm and 355 nm wavelengths respectively, which enter the detection device in sequence. The laser beams of abovementioned three wavelengths are commonly used by ground and spaceborne radars for atmospheric aerosol detection, crossing 1064 nm near-infrared band, 532 nm visible light band and 355 nm ultraviolet band, and the use of these three wavelengths is favorable to the wider application in late-stage atmospheric sounding. Also, the light source provided by the light path device of the present invention can also be provided by a plurality of single-wavelength lasers, for example, three single-wavelength lasers can be used to provide laser beams of 870 nm, 405 nm and 781 nm respectively. If necessary, a laser of single wavelength can be selected, for example, only for the measurement of 1064 nm fundamental wavelength, the aerosol optical characteristics at 1064 nm wavelength are measured without needing frequency division or frequency multiplication. In a preferable embodiment of the present invention, the laser beam of 1064 nm wavelength is divided into laser beams of 1064 nm, 532 nm and 355 nm by frequency-multiplying crystals, so as to achieve the purpose of multi-channel measurement.

Wherein, said laser modulation unit comprises a frequency multiplication unit, a frequency division unit and a light coupling unit, which are connected in sequence.

In particular, said frequency multiplication unit comprises a chopper, a first lens, a first LBO frequency-tripling crystal, a second lens and a second LBO frequency-tripling crystal, which are arranged in sequence, wherein the laser beam of 1064 nm wavelength from the laser transmission unit is frequency-modulated by the chopper and then goes through the first lens and first LBO frequency-tripling crystal in sequence, resulting in laser beams of 1064 nm and 532 nm wavelengths, and said laser beams of 1064 nm and 532 nm go through the second lens and second LBO frequency-tripling crystal in sequence, resulting in laser beams of 1064 nm, 532 nm and 355 nm wavelengths, wherein the LBO frequency-tripling crystals used are frequency-tripling crystals $LiB_3O_5$ which can divide the laser beam of 1064 nm wavelength outputted from the fundamental frequency laser into laser beams of 1064 nm, 532 nm and 355 nm wavelengths and have wide transmission band range, high damage threshold and large acceptance angle, and an anti-reflection coating (anti-reflection film) is formed on the surface of each LBO frequency-tripling crystal.

Said frequency division unit comprises a third lens, a fourth lens, a fifth lens, a first beam splitter, a second beam splitter, a first light chopper, a second light chopper and a third light chopper. The laser beam from the frequency multiplication unit goes through the third lens and first beam splitter in sequence, so that the laser beam is divided into a first light beam and a second light beam, wherein the first light beam goes through the first light chopper to form a laser beam of 355 nm wavelength, the second light beam goes through the fourth lens and second beam splitter in sequence so that the laser beam is divided into a third light beam and a fourth light beam, wherein said third light beam goes through the second light chopper to form a laser beam of 532 nm wavelength, and the fourth light beam goes through the fifth lens and third light chopper to form a laser beam of 1064 nm wavelength.

Said light coupling unit comprises a sixth lens, a seventh lens, an eighth lens, a ninth lens, a tenth lens, an eleventh lens, a twelfth lens, a thirteenth lens, a first folding mirror, a second folding mirror, a third folding mirror, a light coupler and a light collimator, wherein the laser beam of 355 nm wavelength from the light path device goes through the sixth lens, first folding mirror and seventh lens in sequence and then enters the light coupler, the laser beam of 532 nm wavelength from the light path device goes through the eighth lens, second folding mirror and ninth lens in sequence and then enters the light coupler, the laser beam of 1064 nm wavelength from the light path device goes through the tenth lens, third folding mirror and eleventh lens in sequence and then enters the light coupler, and the three laser beams of different wavelengths enter the light coupler in sequence, then enter the light collimator after going through the twelfth lens in sequence and finally enter the detection device after going through the thirteenth lens. Preferably, the number of the photoelectric detectors positioned on the surface of the photoacoustic cavity is five, being a first photoelectric detector, a second photoelectric detector, a third photoelectric detector, a fourth photoelectric detector and a fifth photoelectric detector respectively, wherein the detection angle of the first photoelectric detector ranges from 3° to 177°, the detection angle of the second photoelectric detector ranges from 33° to 147°, the detection angle of the third photoelectric detector ranges from 1° to 179°, the detection angle of the fifth photoelectric detector ranges from 55° to 125°, and the five photoelectric detectors are mounted on the inner surface of the photoacoustic cavity in terms of the detection angles. In order to ensure the accuracy of aerosol scattering phase function measurement, at least four photoelectric detectors are needed, the number of photoelectric detectors can be appropriately increased in case that the space is enough, but more photoelectric detectors are not the best because more photoelectric detectors may change the intrinsic frequency of the detection cavity, resulting in adverse effects, therefore, the number is preferably 4-10.

Said sample loading unit comprises an aerosol cutting head, a flow meter, three-way valves and a mass flow meter, which are connected in sequence, and said aerosol sampling gas flow firstly goes through the aerosol cutting head and flow meter and then enters the detection device after going through the three-way valves and mass flow meter, wherein a temperature/pressure/humidity sensor is arranged between said three-way valves and said mass flow meter.

Said calibration unit comprises a zero gas generator, a first calibration gas source and a second calibration gas source, wherein a zero gas from the zero gas generator, a first calibration gas from the first calibration gas source and a second calibration gas from the second calibration gas source go through the mass flow meter respectively and then enter the detection unit.

Said sample discharging unit comprises a mass flow meter, a flow meter and a pump, which are connected in sequence, and the gas flow going through the detection unit goes through the mass flow meter and flow meter in sequence and then is discharged from the detection unit under the pulling action of the pump, wherein a temperature/pressure/humidity sensor is arranged between said mass flow meter and flow meter.

Said multi-channel aerosol scattering absorption measuring instrument is provided with a temperature control unit. Said temperature control unit comprises a double-layer stainless steel case body, semiconductor refrigerators, heat-exchange fans and a temperature/pressure/humidity sensor, wherein said double-layer stainless steel case body is mounted outside said detection device, said semiconductor refrigerators, heat-exchange fans and temperature/pressure/humidity sensor are arranged on the surface of the double-layer stainless steel case body, respectively, a window is formed on one side of said double-layer stainless steel case body so that a light source from the light path device enters said detection device, the data of said temperature/pressure/humidity sensor is transmitted to the control device, and according to the transmitted data, the control device determines whether to start the semiconductor refrigerators and heat-exchange fans to control the temperature in the double-layer stainless steel case body.

Said multi-channel aerosol scattering absorption measuring instrument is provided with an inlet gas sound insulation device and an exhaust gas sound insulation device, wherein said inlet gas sound insulation device comprises a first buffer, a first sound filter and a second buffer, which are connected in sequence, wherein said first buffer is mounted to the exit of the sample loading unit and connected to a first receiver, and said second buffer constitutes one end of said photoacoustic cavity, and said exhaust gas sound insulation device comprises a third buffer, a second sound filter and a fourth buffer, wherein said third buffer is mounted to the entrance of the sample discharging unit and connected to a second receiver, and said fourth buffer constitutes the other end of said photoacoustic cavity.

Each lens of the present invention is arranged so that the color dispersion can be eliminated when the laser beam reach the next stage after going through the crystals or subjecting to optical conversion at each time and the light path can enter the next stage in a way of beam concentration as much as possible. In order to achieve better effects, each lens needs to be coated with an anti-reflection film, so that the transmittance thereof exceeds 99.9%. The lenses may be made of plastic or glass, and plastic lenses are preferred for the purpose of cost reduction. In order to meet the requirement that the space can accommodate the devices, total reflectors and lenses can be used in the system to change the travel direction of light path.

Advantageously, compared with the prior art, the multi-channel aerosol scattering absorption measuring instrument of the present invention can not only directly measure the scattering phase function and absorption coefficient of aerosols but also achieve multi-channel (three wavelengths), multi-angular, full-scale (0.001-100 μm) photoacoustic/spectral synchronous on-line direct measurement of aerosol scattering phase function and absorption coefficient, which fully covers the whole scattering spatial intensity distribution of aerosol particles and precisely acquires aerosol scattering coefficient, extinction coefficient, transmittance, visibility and single scattering albedo on the basis of accurately acquiring aerosol scattering phase function and absorption coefficient, thereby achieving synchronous integrated acquisition of all optical characteristics of aerosols.

DESCRIPTION OF DRAWINGS

FIGS. 4($a$), 4($b$), 4($c$) and 4($d$) represent aerosol particle scattering phase functions at effective radii of 0.18 um, 0.44 um, 0.60 um and 0.74 um, respectively.

PARTICULAR EMBODIMENTS

The present invention can be better understood with reference to the following examples. However, it should be apparent to those skilled in the art that the specific examples are given by way of illustration only, without implying any limitation to the detailed description in claims of the invention.

The multi-channel aerosol scattering absorption measuring instrument of the present invention mainly comprises a light path device A, a detection device B, a gas path device C, a temperature control unit, an inlet gas sound insulation device and an exhaust gas sound insulation device.

Figure 1:
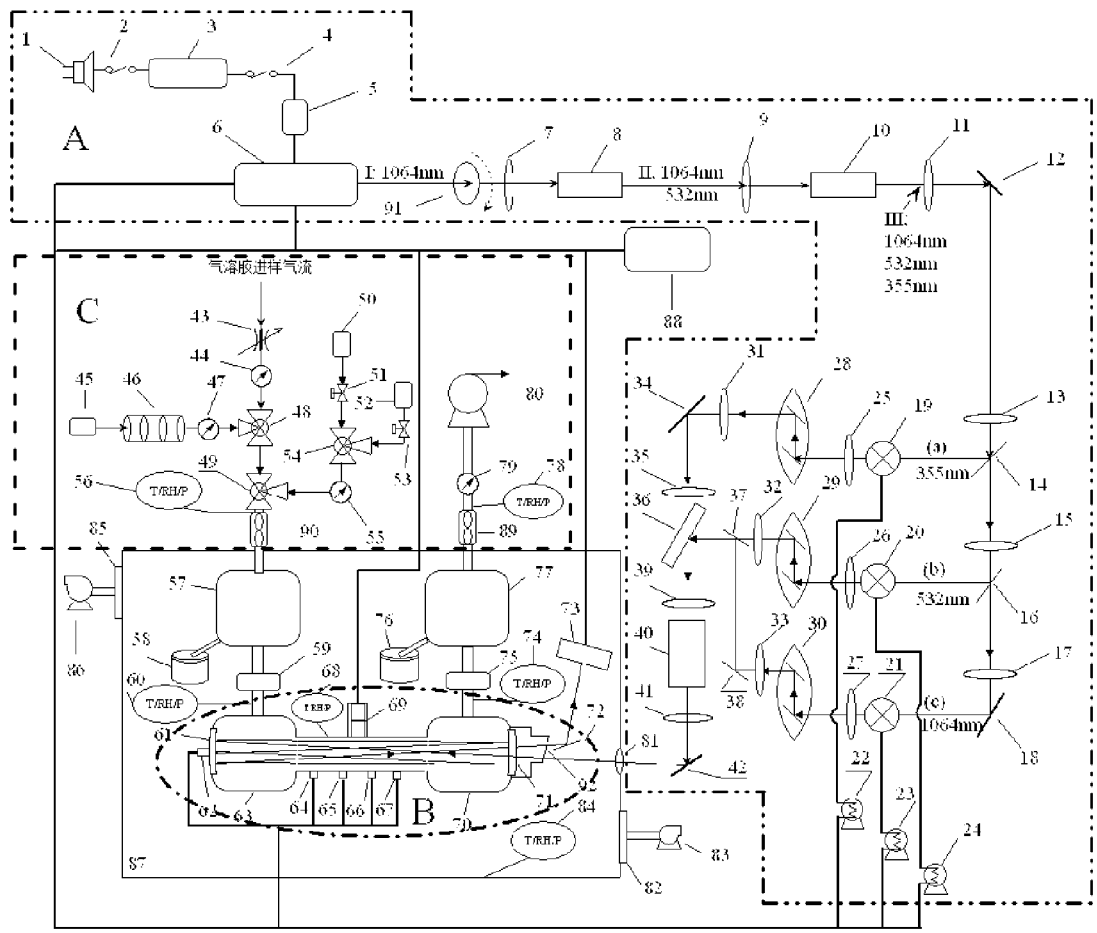
FIG. 1 is a schematic diagram of structure of the multi-channel aerosol scattering absorption measuring instrument of the present invention.

The light path device comprises a laser transmission unit and a laser modulation unit, which are connected in sequence. Wherein, as shown in FIG. 1, the laser transmission unit comprises a power supply (1), a switch (2), a voltage stabilizer (3), a switch (4), a laser controller (5) and a laser (6); after the switch (2) is actuated, the voltage stabilizer (3) is powered; after the switch (4) is actuated, and the laser controller (5) controls the laser (6) to output a laser beam of 1064 nm fundamental frequency wavelength. The voltage stabilizer (3) is adopted to ensure power supply voltage for the laser.

The laser modulation unit comprises a frequency multiplication unit, a frequency division unit and a light coupling unit, which are connected in sequence, wherein the frequency multiplication unit comprises a chopper (91), a first lens (7), a first LBO frequency-tripling crystal (8), a second lens (9) and a second LBO frequency-tripling crystal (10), which are connected in sequence. The LBO frequency-tripling crystals used are frequency-tripling crystals $LiB_3O_5$ which can divide the laser beam of 1064 nm wavelength from a fundamental frequency laser into laser beams of 1064 nm, 532 nm and 355 nm wavelengths and have wide transmission band range, high damage threshold and large acceptance angle, and an anti-reflection coating (anti-reflection film) is formed on the surface of each LBO frequency-tripling crystal. Wherein, the frequency of the fundamental frequency laser beam of 1064 nm wavelength from the laser transmission unit is up-modulated by the chopper (91) to 1500 Hz, so that the laser transmission unit outputs a stable laser beam of 1064 nm fundamental wavelength as required, which go through the first lens (7) and first LBO frequency-tripling crystal (8) in sequence to form laser beams of 1064 nm and 532 nm wavelengths, and the laser beams of 1064 nm and 532 nm wavelengths go through the second lens (9) and second LBO frequency-tripling crystal (10) in sequence to form laser beams of 1064 nm, 532 nm and 355 nm wavelengths. One fourteenth lens (11) and a first total reflector (12) are arranged between the frequency multiplication unit and frequency division unit. The arrangement of the lens ensures that the color dispersion can be eliminated when the laser beam reach the next stage after going through the LBO frequency-tripling crystals or subjecting to optical conversion at each time and makes the light path enter the next stage in a way of beam concentration as much as possible. The total reflector is used to change the direction of the system light path.

The frequency division unit comprises a third lens (13), a fourth lens (15), a fifth lens (17), a first beam splitter (14), a second beam splitter (16), a first light chopper (19), a second light chopper (20) and a third light chopper (21). The laser beam from the frequency multiplication unit firstly goes through the third lens (13) and first beam splitter (14) in sequence so that the laser beam is divided into a first light beam and a second light beam, wherein the first light beam goes through the first light chopper (19) to form a laser beam of 355 nm wavelength, the second light beam goes through the fourth lens (15) and second beam splitter (16) in sequence so that the laser beam is divided into a third light beam and a fourth light beam, wherein said third light beam goes through the second light chopper (20) to form a laser beam of 532 nm wavelength, and the fourth light beam goes through the fifth lens (17) and the third light chopper (21) to form a laser beam of 1064 nm wavelength, and one second total reflector (18) is arranged between the fifth lens (17) and third light chopper (21) to change the direction of light path and facilitate the placement of devices. The purpose of frequency division is to control the laser wavelength of each channel. The frequency is modulated using the chopper (91) to meet the measurement requirement of the photoacoustic cavity and satisfy the result of aerosol absorption coefficient measurement via a sound converter (69), and interference on measurement of photoacoustic signals of three paths of laser beams is eliminated. Also, the wavelength division of three paths of laser beams allows the independent operation of scattered light detection and transmittance detection, so as to acquire aerosol scattering signal and transmittance signal of each path of laser beam.

The light coupling unit comprises a sixth lens (25), a seventh lens (31), an eighth lens (26), a ninth lens (32), a tenth lens (27), an eleventh lens (33), a twelfth lens (39), a thirteenth lens (41), a first folding mirror (28), a second folding mirror (29), a third folding mirror (30), a light coupler (36) and a light collimator (40), wherein, the laser beam of 355 nm wavelength from the light path device goes through the sixth lens (25), first folding mirror (28) and seventh lens (31) in sequence and then enters the light coupler (36), wherein, a third total reflector (34) and a fifth lens (35) are arranged between the seventh lens (31) and light coupler (36) to change the light path direction and enable the light beam to enter the light coupler (36) in a way of concentration, the laser beam of 532 nm wavelength from the light path device goes through the eighth lens (26), second folding mirror (29) and ninth lens (32) in sequence and then enters the light coupler (36), and the laser beam of 1064 nm wavelength from the light path device goes through the tenth lens (27), third folding mirror (30) and eleventh lens (33) in sequence and then enters the light coupler (36), and a fourth total reflector (38) and a mirror (37) are arranged between the eleventh lens (33) and light coupler (36), wherein the mirror (37) can transmit the second path of laser beam and totally reflect the third path of laser beam, so as to change the direction of the third path of laser beam, as a result, the third path of laser beam is coaxial to the second path of laser beam. By the arrangement of the fourth total reflector (38) and mirror (37), the purpose of changing the light path direction and enabling the light beams to enter the light coupler (36) in a way of concentration is achieved. The three paths of laser beams with different wavelengths enter the light coupler (36) in sequence, then enter the light collimator (40) after going through the twelfth lens (39), and finally enter the detection device after going through the thirteenth lens (41) and one fifth total reflector (42). The light coupling unit is adopted to allow the three paths of laser beams to coaxially enter the measurement system in sequence. The frequency modulation of the three paths of laser beams are controlled by a first stepping motor (22), a second stepping motor (23) and a third stepping motor (24), respectively, the three paths of laser beams are chopped and blocked step by step via the first light chopper (19), second light chopper (21) and light chopper (20), so that only one path of laser beam enters a scattering phase function and absorption coefficient detection cavity at each time, and the photoelectric detectors and photoacoustic cavity measure scattering phase function and absorption signal of only one wavelength at each time, thereby acquiring all optical parameters of aerosols.

In the invention, each lens is arranged so that the color dispersion can be eliminated when the laser beams reach the next stage after going through the crystals or subjecting to optical conversion at each time and the light path can enter the next stage in a way of beam concentration as much as possible. In order to achieve better effects, each lens needs to be coated with an anti-reflection film, so that the transmittance thereof exceeds 99.9%. The lenses may be made of plastic or glass, and plastic lenses are preferred for the purpose of cost reduction.

Figure 2:
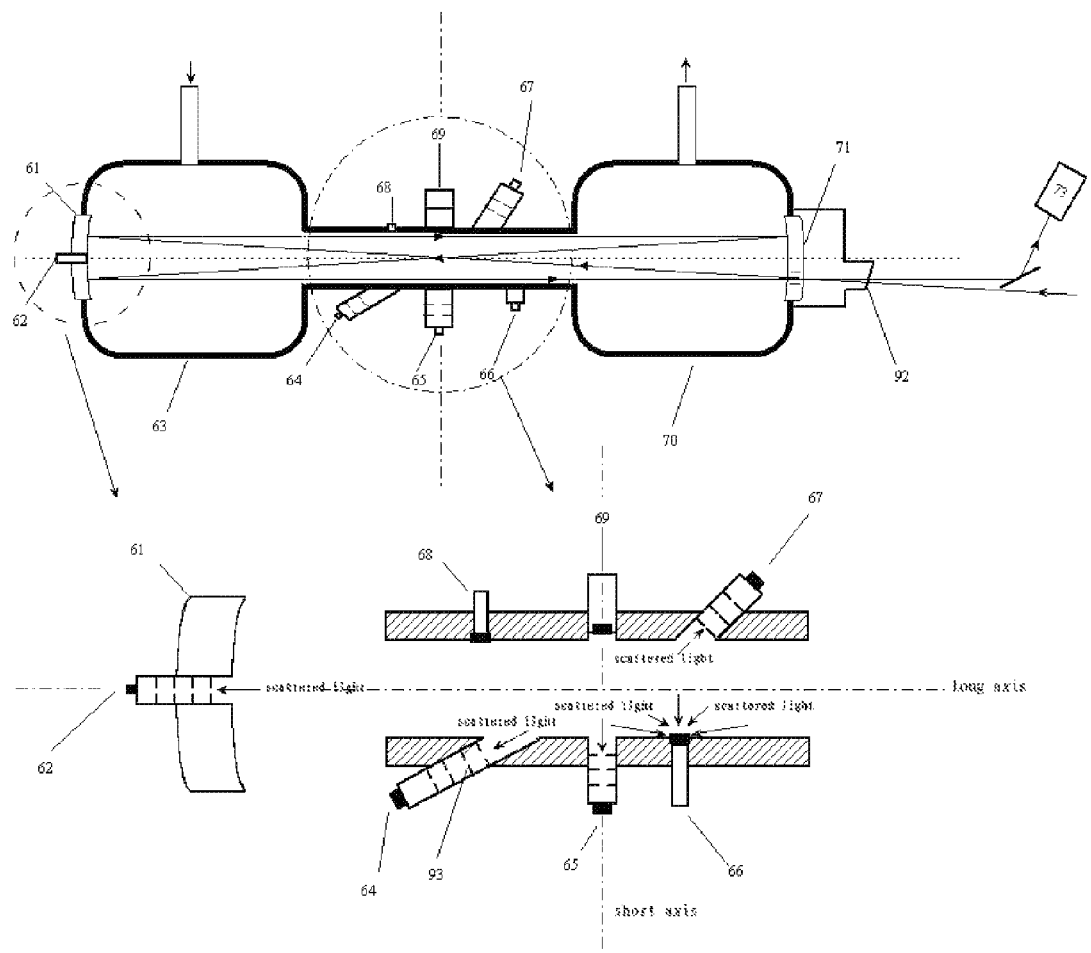
FIG. 2 is a schematic diagram of mounting position and partial approach of the photoelectric detectors.
Figure 3:
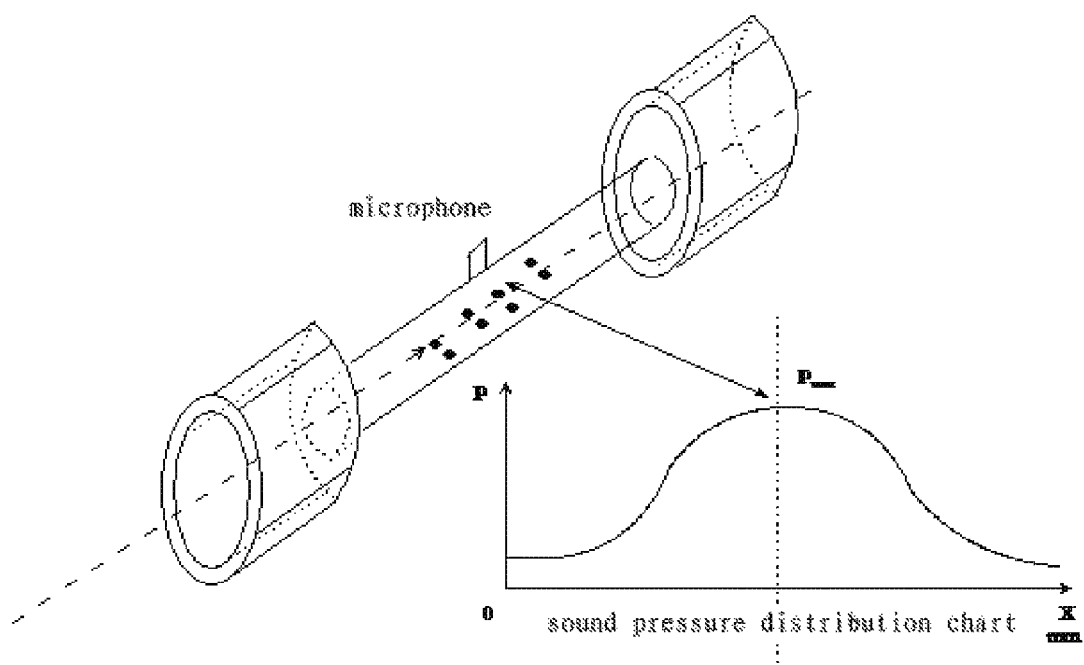
FIG. 3 illustrates the scattering phase function and absorption detection cavity and sound pressure intensity distribution.

The detection device comprises a control unit and a detection unit, wherein the detection unit comprises a photoacoustic cavity, a first long-range multiple reflector (71), a second long-range multiple reflector (61), a first temperature/pressure/humidity sensor (68), the sound converter (69) and a first photoelectric detector (62), a second photoelectric detector (64), a third photoelectric detector (65), a fourth photoelectric detector (66), a fifth photoelectric detector (67) and a sixth photoelectric detector (73). Wherein, the first long-range multiple reflector (71) and second long-range multiple reflector (61) are positioned at the two ends of the photoacoustic cavity respectively, the first long-range multiple reflector (71) and second long-range multiple reflector (61) have the same reflection principle as Herriott optical long-range cells, the reflection results in a hollow cylindrical pillar formed by the light path between the two long-range multiple reflectors, so that a cavity is formed between the two long-range multiple reflectors, and the photoacoustic cavity covers the two long-range multiple reflectors to form a detection cavity. Wherein, the sixth photoelectric detector (73) is arranged outside the light source emergence port of the detection unit in a way of corresponding to the emergence direction of the light source and is connected to the control unit (88), other photoelectric detectors are arranged on the surface of the photoacoustic cavity (shown as FIG. 2) for measurement angles of 3° and 177°, 33° and 147°, 90°, 1° to 179° and 55° and 125°, in the figure, the black square parts represent the detection faces of the detectors, and in order to allow the aerosol scattered light of only one direction to enter the photoelectric detectors, the incident light parts of other photoelectric detectors than the photoelectric detector (66) having measurement angle of 1° to 179° are provided with a plurality of light-limiting partition plates (93) having blocking effect, and holes are formed in the middle of the partition plates, as a result, the aerosol scattered light of only one direction is allowed to enter. Wherein, the first photoelectric detector (62) having measurement angle of 3° and 177° is arranged at the axial end of the second long-range multiple reflector (61), the second photoelectric detector (64) having measurement angle of 33° and 147°, fifth photoelectric detector (67) having measurement angle of 55° and 125° and fourth photoelectric detector (66) having measurement angle of 1° to 179° are arranged on both sides of the middle part of the photoacoustic cavity, the third photoelectric detector (65) having measurement angle of 90° is arranged on the inner surface of the middle part of the photoacoustic cavity and perpendicular to the central axis of the photoacoustic cavity, the included angles from the symmetric axes of the second photoelectric detector (64), fifth photoelectric detector (67) and third photoelectric detector (65) to the long axis of body of the photoacoustic cavity are 33°/147°, 55°/125° and 90° respectively, and the detection face of the fourth photoelectric detector (66) slightly enters the photoacoustic cavity and is perpendicular to the long axis of the cavity body, so as to measure the scattered light of 1° to 179°. The first temperature/pressure/humidity sensor (68) and sound converter (69) are arranged on the inner surface of said photoacoustic cavity respectively, the sound converter (69) is arranged in the middle position of the photoacoustic cavity and perpendicular to the long axis of the cavity body, and the probe of the first temperature/pressure/humidity sensor (68) slightly enters the body of the photoacoustic cavity, so as to measure temperature/pressure/humidity parameters in the cavity body. In case that the space is enough, the five photoelectric detectors and first temperature/pressure/humidity sensor (68) can all be positioned on the central cross-section perpendicular to the long axis of the cavity body (on the same plane as the short axis in FIG. 2), that is, on the same plane as the sound converter (69), but at different angles. The first temperature/pressure/humidity sensor (68), sound converter (69) and all the photoelectric detectors are connected to said control unit (88) separately. The sound converter (69) is arranged to accurately acquire the absorption coefficient of an aerosol. In The first temperature/pressure/humidity sensor (68) can monitor the environmental conditions inside the photoacoustic cavity and also plays an important role of instrument calibration and processing of detection signals. The use of the first photoelectric detector (62) having measurement angle of 3° and 177° is to acquire the measurement result of paraxial narrow-angle forward/backward scattering, the second photoelectric detector (64), fifth photoelectric detector (67) and third photoelectric detector (65) measure the scattered light at different angles, so as to accurately acquire the aerosol scattering phase function, and the photoelectric detector (66) for total scattering coefficient measurement is used to acquire the aerosol total scattering coefficient of 1-179°. The detection angle of each photoelectric detector can be adjusted finely and appropriately. Aerosol particles having different particle sizes show different scattering intensities under the exposure to laser beams of different wavelengths, and the scattering coefficient is acquired on the basis of measurement of scattering intensity distribution (i.e. phase function). Since different particles show different scattering profiles along with different wavelengths, generally, it is needed to measure the scattering angles sensitive to intensity distribution, therefore, fine adjustment is allowed according to the arrangement requirement and the practical situation of body space of the photoacoustic cavity. The detection cavity (photoacoustic cavity) has a cylindrical structure, so that, on the one hand, the requirement for arrangement of all detection devices can be satisfied, and on the other hand, the use of cylindrical structure can enhance signals for direct measurement of aerosol absorption. FIG. 3 shows the arrangement position of the sound converter (69) (i.e. microphone or mike), in which X represents the length of the photoacoustic cavity, FIG. 3 also shows the curve of change of sound pressure distribution curve P along with the change in length of the photoacoustic cavity, the sound converter (69) is arranged in the position of maximum sound pressure, that is, the middle position of the photoacoustic cavity. The detection principle of the photoacoustic cavity is that when the aerosol particles are exposed to the light, the particles absorb light energy to produce sound pressure and light-sound interconversion. As the value of sound pressure resulting from light energy absorption of a sample is measured by photoacoustic spectrometry, the interference of reflected light and scattered light on the measurement is reduced. The first long-range multiple reflector (71) and second first long-range multiple reflector (61) are implanted into the photoacoustic cavity, so as to greatly enhance detection signals of the sound converter and also make the measurement of transmittance easier. The sound converter (69) is a detection sensor for direct measurement of aerosol absorption coefficient. In order to enclose incident/emergent light and prevent the loss of calibration gas and sample gas, a window (72) is formed at the end of the photoacoustic cavity where the first long-range multiple reflector (71) is positioned, through which the laser beams from the light path device go. The detection principle of the photoelectric detectors is that when the laser beam goes and returns between the first long-range multiple reflector (71) and second long-range multiple reflector (61) in the detection unit, the signal of the sound converter can be enhanced as well as the detection signal of each aerosol scattered light can be greatly enhanced. Wherein, under the action of a fifth total reflector (42), the incident light goes through a window (81) and window (92), enters the edge of the first long-range multiple reflector (71) and reaches the corresponding edge of the second first long-range multiple reflector (61), and finally, in this manner, emerges after multiple reflection (the number of reflection is determined by the relative torsion angle between the first long-range multiple reflector (71) and second long-range multiple reflector (61) and the area, thickness, concavity, curvature radius and spacing of the first long-range multiple reflector (71) and second long-range multiple reflector (61), in particular, the number of reflection can be adjusted according to the real size of the detection cavity of the instrument). The first long-range multiple reflector (71) and second long-range multiple reflector (61) in combination with the photoelectric detector (73) can achieve the measurement of transmittance. The multiple reflection results in a cavity formed by the light path inside the detection cavity, so that the first photoelectric detector (62) can be mounted on the symmetric axis of the second long-range multiple reflector (61), and the measurement of intensity of narrow-angle paraxial forward/backward scattering can be achieved. In the above-mentioned scattering measurement scheme, with the measurement results of the first to the fifth photoelectric detectors, the profile of aerosol scattering angle distribution can be fully acquired, leading to the measured curve of scattering phase function of aerosol.

The first photoelectric detector (62) is mounted on the symmetric axis of the second long-range multiple reflector (61), and the second to the fifth photoelectric detectors can be mounted on the same axial plane as the central symmetric axis of the photoacoustic cavity, the mounting angles being adjusted if necessary.

The gas path device comprises a sample loading unit, a calibration unit and a sample discharging unit, wherein the sample loading unit and sample discharging unit communicate with the two ends of said photoacoustic cavity respectively. The sample loading unit comprises an aerosol cutting head (43), a flow meter (44), a first three-way valve (48), a second three-way valve (49), and a first mass flow meter (90). Said aerosol sample loading gas firstly goes through the aerosol cutting head (43) and flow meter (44), then goes through the first three-way valve (48), second three-way valve (49) and first mass flow meter (90), and enters the detection device. A second temperature/pressure/humidity sensor (56) is arranged between the second three-way valve (49) and first mass flow meter (90). The calibration unit comprises a zero gas generator (45), a first calibration gas source (50) and a second calibration gas source (55). A zero gas from the zero gas generator (45) firstly goes through a high-efficiency filter (46) and a second flow meter (47) which are connected to the zero gas generator in sequence, and then enters the detection system through the first three-way valve (48), second three-way valve (49) and first mass flow meter (90). A first calibration gas from the first calibration gas source (50) goes through a third three-way valve (51), a fourth three-way valve (54) and a third mass flow meter (55) which are connected to the first calibration gas source, then goes through the second three-way valve (49) and first mass flow meter (90), and enters the detection device. A second calibration gas from the second calibration gas source (52) goes through a fifth three-way valve (53) and the fourth three-way valve (54), then goes through the third mass flow meter (55) and first mass flow meter (90), and enters the detection unit. The sample discharging unit comprises a second mass flow meter (89), a fourth flow meter (79) and a pump (80). A gas flow going through the detection unit goes through the second mass flow meter (89) and fourth flow meter (79) in sequence, and then is discharged from the detection unit under the pulling action of the pump (80), wherein, a temperature/pressure/humidity sensor (78) is arranged between the second mass flow meter (89) and fourth flow meter (79). The temperature/pressure/humidity sensor is a sensor integrating the function of measuring temperature, pressure and humidity, and this temperature/pressure/humidity sensor can also be replaced by a temperature sensor, pressure sensor and humidity sensor working alone, for the detection of temperature, pressure and humidity in the system environment. As the spectrum of aerosol particles ranges from to 0.001 μm to 100 μm, the entrance of sampling aerosol flows is controlled using aerosol cutting heads having different sizes, so that the particle size of aerosol which finally enters the cavity is desired. For the sample loading gas flow, the flow measurement is required and performed using the flow meters and mass flow meters, the temperature/pressure/humidity measurement is also required. The three-way valves are used for switching between the aerosol measurement model and the calibration model. The sample discharging unit and sample loading unit are relatively simple. Especially, after going through the scattering absorption measurement system, the aerosol is discharged from the measurement system under the pulling action of the pump (80). In addition to flow monitoring and mass monitoring, temperature/pressure/humidity detection is required. With these parameters together with the related measurement results of the sample loading system, the difference and relationship between the sample loading flow and sample discharging flow can be acquired during the measurement of scattering and absorption characteristics of aerosol in the present invention. The light source from the light path device and the gas flow from the gas path device enter the photoacoustic cavity and are detected by the control unit respectively.

The temperature control unit comprises a double-layer stainless steel case body (87), a first semiconductor refrigerator (82), a second semiconductor refrigerator (85), a first heat-exchange fan (83), a second heat-exchange fan (86), and a temperature/pressure/humidity sensor (84), wherein the double-layer stainless steel case body (87) is arranged outside the detection device, the first semiconductor refrigerator (82), second semiconductor refrigerator (85), first heat-exchange fan (83), second heat-exchange fan (86) and temperature/pressure/humidity sensor (84) are arranged on the surface of said double-layer stainless steel case body (87) respectively, the first semiconductor refrigerator (82) and first heat-exchange fan (83) are arranged on the side wall at one corner of the double-layer stainless steel case body (87) and the second semiconductor refrigerator (85) and second heat-exchange fan (86) are arranged on the side wall of the opposite corner, so that the measurement results are more uniform, the window (81) is formed on one side of the double-layer stainless steel case body (87) so that the light source from the light path device goes through the fifth total reflector (42), window (81) and window (92) in sequence, the three paths of laser beams go through the window (81) and enter the detection unit in sequence, the light paths go and return for several times between the first long-range multiple reflector (71) and second long-range multiple reflector (61) in the cavity body, and then emerge through the light source emergence port (also light source incidence port) and reach a sixth total reflector (72) which is arranged outside the window of the detection unit, and the emergent light paths reach the photoelectric detector (73) via the sixth total reflector (72). By the integration of scattering measurement and absorption measurement of aerosol in the same one detection cavity, the errors resulting from different background signals of different cavity bodies can be eliminated. Also, the three paths of laser beams enter the detection system in sequence with no inter-interference. The detected data of the temperature/pressure/humidity sensor is transmitted to the control unit. According to the transmitted data, the control unit determines whether to start the first semiconductor refrigerator (82), second semiconductor refrigerator (85), first heat-exchange fan (83) and second heat-exchange fan (86) to control the temperature in the double-layer stainless steel case body (87). The temperature control unit is used to overcome the problem that the temperature of the measurement system rises due to frequent photoelectric/photoacoustic conversion, the double-layer stainless steel case body (87) is used to insulate heat of the whole measurement unit (sound-insulating heat-insulating materials are filled between the two layers), the fourth temperature/pressure/humidity sensor (84) is used to monitor the change in temperature inside the case body, the first heat-exchange fan (83) and second heat-exchange fan (86) are started or stopped in time, the semiconductor refrigerators (82) and (85) are used to cool the case body, thereby achieving the purpose of ensuring normal operation of the measurement system.

The inlet gas sound insulation device comprises a first buffer (57), a first sound filter (59) and a second buffer (63), which are connected in sequence, wherein the first buffer (57) is mounted to the exit of the sample loading unit and connected to a first receiver (58), and the second buffer (63) constitutes the end where the second long-range multiple reflector (61) is located. The exhaust gas sound insulation device comprises a third buffer (77), a second sound filter (75) and a fourth buffer (70), wherein the third buffer (77) is mounted to the entrance of the sample discharging unit and connected to a second receiver (76), and the fourth buffer constitutes the other end of the photoacoustic cavity. A fifth temperature/pressure/humidity sensor (60) is arranged on a pipe between the first sound filter (59) and second buffer (63), and a sixth temperature/pressure/humidity sensor (74) is arranged on a pipe between the second sound filter (75) and fourth buffer (70). Sound insulation involves three aspects as follows: one aspect is overall sound insulation of the photoacoustic cavity for measurement, that is, the sound insulation of the whole detection unit is implemented using the double-layer stainless steel case body (87) (sound-insulating heat-insulating materials are filled between the two layers), so as to insulate noise of the external environment; another aspect is insulation of inlet gas sampling flow noise as well as minimization of flow velocity noise of gas flows, the two aspects are implemented using the first sound filter (59), first buffer (57) and second buffer (63) respectively; the other aspect is control of sample discharging gas flow noise, which is implemented using the second sound filter (75), third buffer (77) and fourth buffer (70). The receiver (58) and receiver (76) receive water from the sample loading and discharging gas flows respectively.

The control unit (88) is an instrument measurement and control system comprising a data acquisition card (not shown in the figure) and a data monitoring processing software (not shown in the figure). In the instrument, the laser (6), three choppers, three stepping motors, six temperature/pressure/humidity sensors, six photoelectric detectors, sound converter (69), two semiconductor refrigerators, two heat-exchange fans are all connected to the data acquisition card and control circuit. Said data monitoring software is virtual instrument software (LabVIEW8.6 edition) provided by National Instrument ltd., U.S.A.

The particular procedures of measurement are as follows:

(1) The power switches 2 and 4 are turned on to power the whole system, the self-checking system is actuated, so that the laser (6) outputs the laser beam of fundamental frequency which is divided into three paths of laser beams by the frequency multiplication system and frequency division system.

(2) At the same time, under the control of the first three-way valve (48) and second three-way valve (49), the zero gas from the zero gas generator (45) enters the detection cavity (i.e. photoacoustic cavity, the same below) through the first three-way valve (48) and second three-way valve (49), the first stepping motor (22) is turned on and the second stepping motor (48) and fourth stepping motor are turned off, so that the laser beam of 355 nm wavelength enters the detection cavity through the first light chopper (19), the background signal under this wavelength is detected for calibration use. Herein the parameter measurement refer to the detection of temperature/pressure/humidity, mass flow, scattered photon number, emergent light intensity and absorption coefficient (sound converter: microphone), in which (i) the temperature, pressure and humidity are detected using six temperature/pressure/humidity sensors respectively, (ii) the mass flow detection is carried out using the second mass flow meter (89) and first mass flow meter (90) in sequence, (iii) the numbers of scattered photons in individual positions are detected using the first to fifth photoelectric detectors (photomultiplier tubes, PMT) respectively, (iv) the emergent light intensity is detected using the sixth photoelectric detector (73), and (v) the background cavity absorption coefficient is detected using the sound converter (69).

(3) Under the control of the system control circuit, the second three-way valve (49) and fourth three-way valve (54) are opened to provide the first calibration gas source (50) and second calibration gas source (52) for performing calibration measurement on the laser beam of 355 nm. Herein the measured parameters include temperature/pressure/humidity, mass flow, scattered photon number, emergent light intensity and absorption coefficient (sound converter: microphone or mike), in which (i) the temperature/pressure/humidity are detected using the six temperature/pressure/humidity sensors respectively, (ii) the mass flow is detected using the second mass flow meter (89) and first mass flow meter (90) in sequence, (iii) the numbers of scattered photons in individual positions are detected using the first to fifth photoelectric detectors (photomultiplier tubes, PMT) respectively, (iv) the emergent light intensity is detected using the sixth photoelectric detector (73), and (v) the calibration gas cavity absorption coefficient is detected using the sound converter (69).

Figure 4:
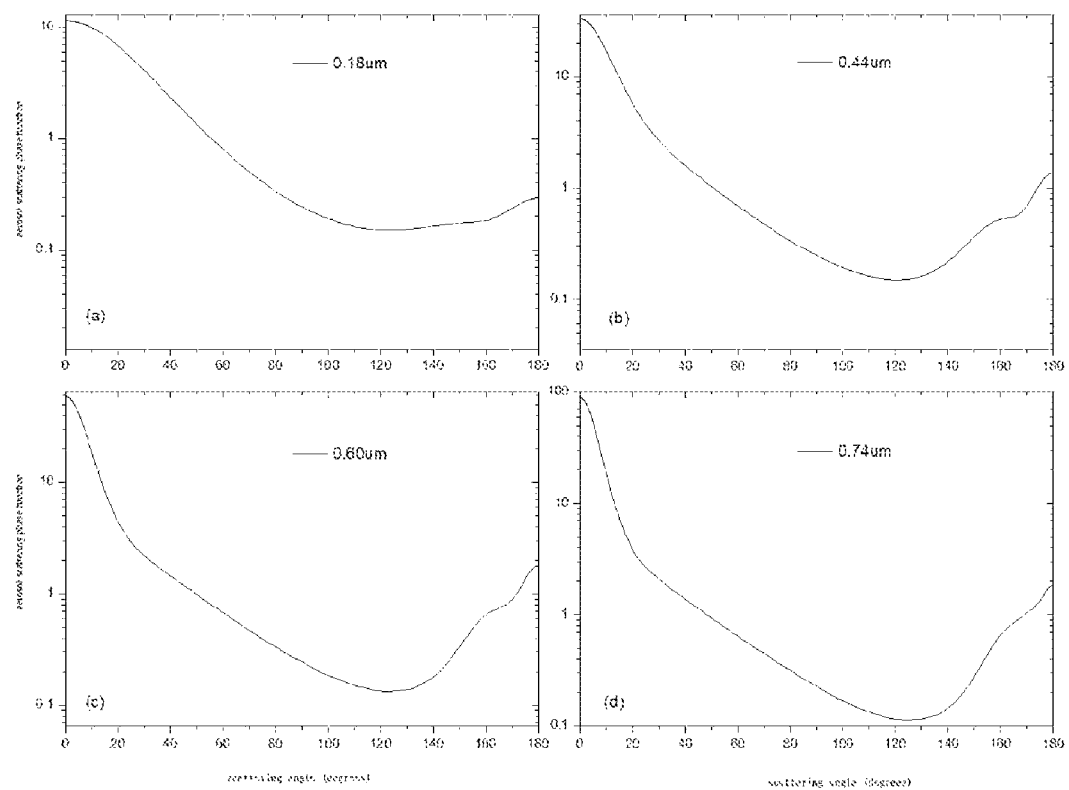
FIG. 4 is a diagram of aerosol particle scattering phase function distribution with different effective radii at 532 nm wavelength of the multi-channel aerosol scattering absorption measuring instrument of the present invention.

(4) The first three-way valve (48) and second three-way valve (49) are turned towards the sample loading gas port, the aerosol particles go through the aerosol cutting head (43) under the action of the pump (80), the aerosol sample flow enters the detection cavity. Herein the measured parameters include temperature/pressure/humidity, mass flow, scattered photon number, emergent light intensity and absorption coefficient (sound converter: microphone or mike), in which (i) the temperature/pressure/humidity are detected using the six temperature/pressure/humidity sensors respectively, (ii) the mass flow detection is performed using the second mass flow meter (89) and first mass flow meter (90) in sequence, (iii) the numbers of scattered photons in individual positions are detected using the first to fifth photoelectric detectors (photomultiplier tubes, PMT) respectively, (iv) the emergent light intensity is detected using the sixth photoelectric detector (73), and (v) the absorption coefficient is detected using the sound converter (69).

(5) The above procedures are carried out periodically to ensure the accuracy of measurement. During the measurement of laser beam of 532 nm wavelength, the second stepping motor (23) is turned on, the first stepping motor (22) and third stepping motor (24) are turned off, the second light chopper (20) is used to enable the laser beam of 532 nm to enter the detection cavity, and the detection process is the same as the laser beam of 355 nm. In the same manner, during the measurement of laser beam of 1064 nm, the third stepping motor (24) is turned on, the first stepping motor (22) and second stepping motor (23) are turned off, and the third light chopper (21) is used to enable the laser beam of 1064 nm to enter the detection cavity. The measurement of parameters related to background and calibration gases is performed once every one day and night, followed by 24-hour sampling measurement. All the detection is automatic.

(6) The above procedures are repeated. However, for measurement verification, the aerosol generator is used to provide aerosol particles of standard shape, for example, aerosol particles having radius of 0.44 micrometers, which enter the detection cavity to measure related parameters.

Detection Algorithm Equations
1 Scattering Coefficient According to the radiation transmission theory, the general expression suitable for both molecules and particles can be obtained:

$$I(\theta) = I_0 \frac{\chi_s}{r^2} \frac{P(\theta)}{4\pi} \quad (1)$$

Wherein $I_0$ represents incident light intensity, $$\chi_s = \frac{\alpha^2 128 \pi^5}{3\lambda^4}$$

represents scattering cross section, $$\alpha = \frac{3}{4\pi N_s}\left(\frac{m^2-1}{m^2+2}\right)$$

represents polarizability, r represents scattering radius, and $P(\theta)$ represents scattering phase function, wherein λ represents incident laser wavelength, $N_s$ represents total amount of molecules or particles per unit volume, $m=m_r-im_i$ represents refractive index of molecules or particles, and $m_r$ and $m_i$ represent real component and imaginary component of molecule or particle refractive index respectively, corresponding to scattering and absorption characteristics of molecules or particles respectively, wherein refractive index is plural, i is representation method of imaginary component, and modulus is 1. FIG. 4 is a diagram of aerosol particle scattering phase function distribution with different effective radii at 532 nm wavelength of the multi-channel aerosol scattering absorption measuring instrument of the invention, wherein FIGS. 4(a), 4(b), 4(c) and 4(d) represent aerosol particle scattering phase functions of aerosol particles at effective radii of 0.18 um, 0.44 um, 0.60 um and 0.74 um, respectively. When aerosol particles of different radii are exposed to the light, different scattering patterns are produced. Since scattering intensity is related to scattering angle, and angular distribution of scattering intensity is in direct proportion to scattering phase function of aerosols, the measurement of scattering phase function is a key factor of scattering intensity measurement in fact, in which, the scattering phase function is a function of scattering angle as well as a non-dimensional parameter.

Therefore, the measurement of scattering coefficient can be represented by a simple equation:

$$\sigma_{sca}^{\lambda} = K_{sca}C - B \quad (2)$$

In the above equation, $K_{sca}$ represents slope of scattering calibration, C represents photon number detected by the photoelectric detectors, and B represents background signal.

$$\sigma_{sca-p}^{\lambda} = \sigma_{sca}^{\lambda} - \sigma_{sca-a}^{\lambda} \quad (3)$$

Figure 5:
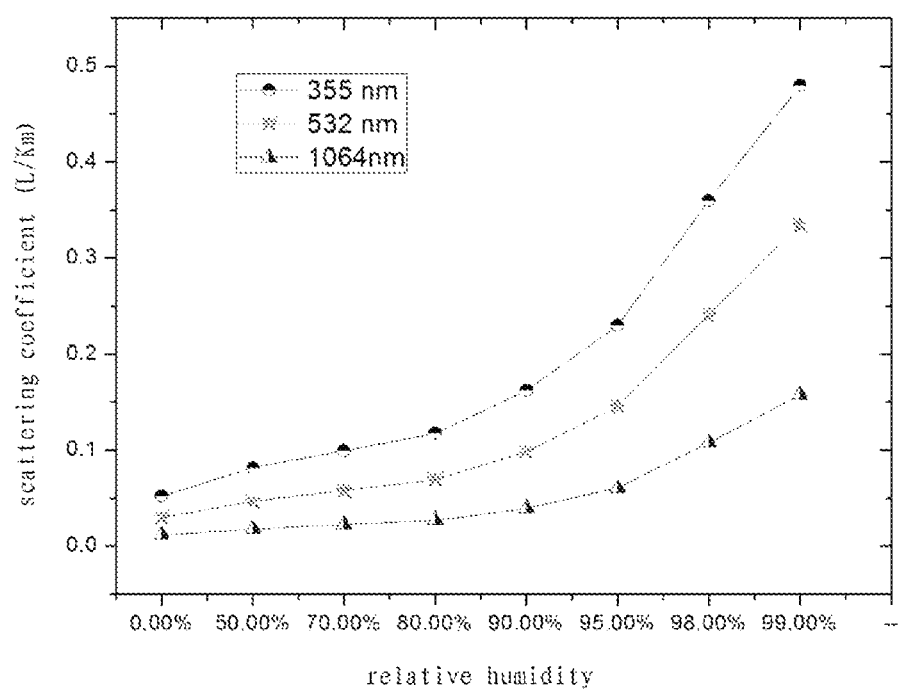
FIG. 5 is a chart of changes in aerosol scattering coefficient along with relative humidity on three channels of 355 nm, 532 nm and 1064 nm wavelengths of the multi-channel aerosol scattering absorption measuring instrument of the present invention.
Figure 6:
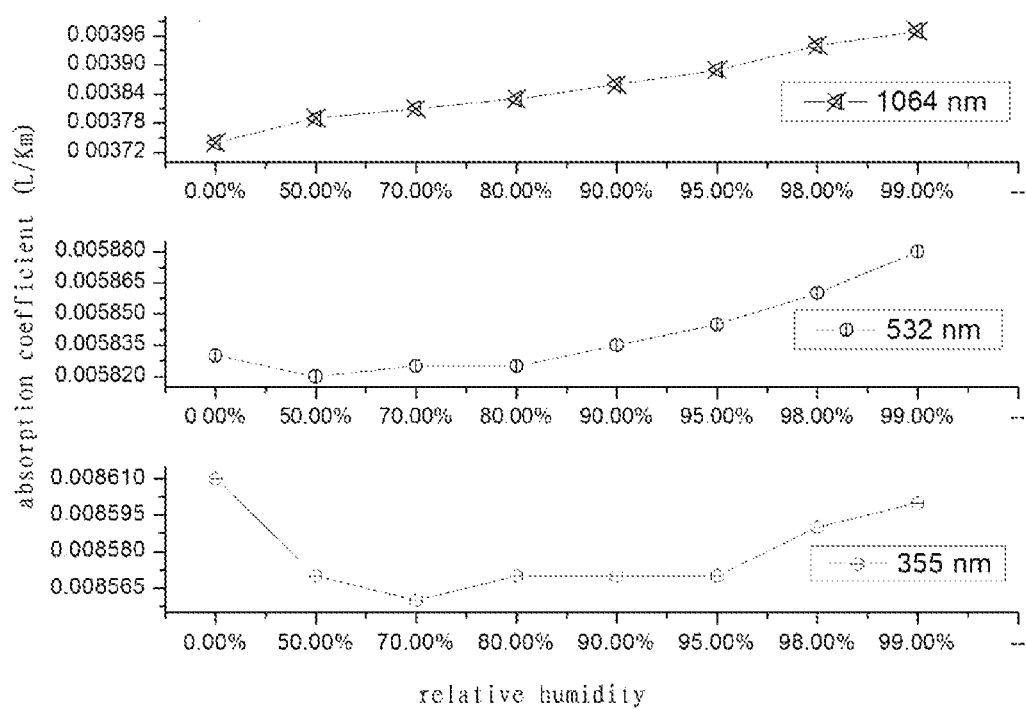
FIG. 6 is a chart of changes in aerosol absorption coefficient along with relative humidity on three channels of 355 nm, 532 nm and 1064 nm wavelengths of the multi-channel aerosol scattering absorption measuring instrument of the present invention.

In the above equation, $\sigma_{sca-p}^{\lambda}$ and $\sigma_{sca-a}^{\lambda}$ a represent aerosol particle scattering coefficient and molecular scattering coefficient, respectively, and $\sigma_{sca-a}^{\lambda}$ is obtained by calculation using a calibration gas and a zero gas during calibration measurement. FIG. 5 is a diagram of changes in aerosol scattering coefficient along with humidity on three channels of 355 nm, 532 nm and 1064 nm wavelengths of the multi-channel aerosol scattering absorption measurement instrument of the invention. In addition to particle spectral distribution of particles and incident laser wavelength, the scattering coefficient of aerosols is also related to atmosphere relative humidity.

2. Absorption Coefficient

Acoustic signals can be represented by the following equation:

$$S = P \cdot M \cdot \left(C \cdot \sum_{i=1}^{n} \eta_i \cdot \alpha_i \cdot c_i + A_b\right) \quad (4)$$

In the above equation, S represents photoacoustic signal intensity (mV), P represents laser power (W), M represents sensitivity of the sound converter (mV·Pa$^{-1}$), C represents photoacoustic cavity constant which is related to cavity geometric parameter, measurement condition and the like (Pa·cm·W$^{-1}$), represents molar absorbance coefficient of each light absorption component entering the cavity under the excitation of λ incident wavelength (cm$^{-1}$·mol$^{-1}$·dm$^3$), $\alpha_i$ represents concentration of each light absorption component (mol·dm$^{-3}$), $\eta_i$ represents efficiency of heat energy conversion from light energy absorbed by each component, $A_b$ represents background signal generation efficiency (Pa·W$^{-1}$), and n represents number of types of all light absorption components.

The photoacoustic cavity constant C can be represented by $$C = \frac{(\gamma-1) \cdot L \cdot Q \cdot G}{f_0 \cdot V} \quad (5)$$

In the above equation, γ represents specific-heat ratio constant measured under isopiestic pressure and isometric volume conditions, L represents length of the optical acoustic cavity (cm), Q represents quality factor, i.e., ratio of Full Width at Half Maximum of resonance frequency to resonance curve, G represents geometric factor, and $f_0$ represents modulation frequency (Hz).

3. Visibility

Atmospheric visibility is represented by the following equation:

$$Vis = \frac{3.912}{\sigma_{ext}^{\lambda}} \quad (6)$$

In the above equation, V is represents visibility, $\sigma_{ext}^{\lambda} = \sigma_{sca-p}^{\lambda} + \sigma_{abs-p}^{\lambda} + \sigma_{sca-a}^{\lambda} + \sigma_{abs-a}^{\lambda}$ represents atmospheric extinction coefficient, being the sum of aerosol scattering coefficient ($\sigma_{sca-p}^{\lambda}$), aerosol absorption coefficient ($\sigma_{abs-p}^{\lambda}$), molecular scattering coefficient ($\sigma_{sca-a}^{\lambda}$) and molecular absorption coefficient ($\sigma_{abs-a}^{\lambda}$). These parameters can be obtained according to the calibration measurement and practical sample measurement, that is, the aerosol scattering phase function can be obtained by measuring the number of scattered photons at multiple angles to obtain aerosol scattering coefficient, the aerosol absorption coefficient is obtained by measurement using the sound converter, and the molecular scattering coefficient and absorption coefficient are obtained by calibration measurement and then calculation.

4. Extinction Coefficient

Extinction coefficient of aerosols can be represented by $\sigma_{ext-p}^{\lambda}$, being the sum of aerosol scattering coefficient ($\sigma_{sca-a}^{\lambda}$) and aerosol absorption coefficient ($\sigma_{abs-p}^{\lambda}$). These parameters can be obtained by calibration measurement and practical sample measurement, that is, the aerosol scattering phase function can be obtained by measuring the number of scattered photons at multiple angles to obtain aerosol scattering coefficient, the aerosol absorption coefficient is obtained by measurement using the sound converter, and the molecular scattering coefficient and absorption coefficient are obtained by calibration measurement and then calculation.

5. Single Scattering Albedo

On the basis of accurate results of aerosol scattering coefficient and absorption coefficient, single scattering albedo $\omega_p^{\lambda}$ of aerosol particles can be obtained and represented by the following equation:

$$\omega_p^{\lambda} = \frac{\sigma_{sca-p}^{\lambda}}{\sigma_{sca-p}^{\lambda} + \sigma_{abs-p}^{\lambda}} \quad (7)$$

Figure 7:
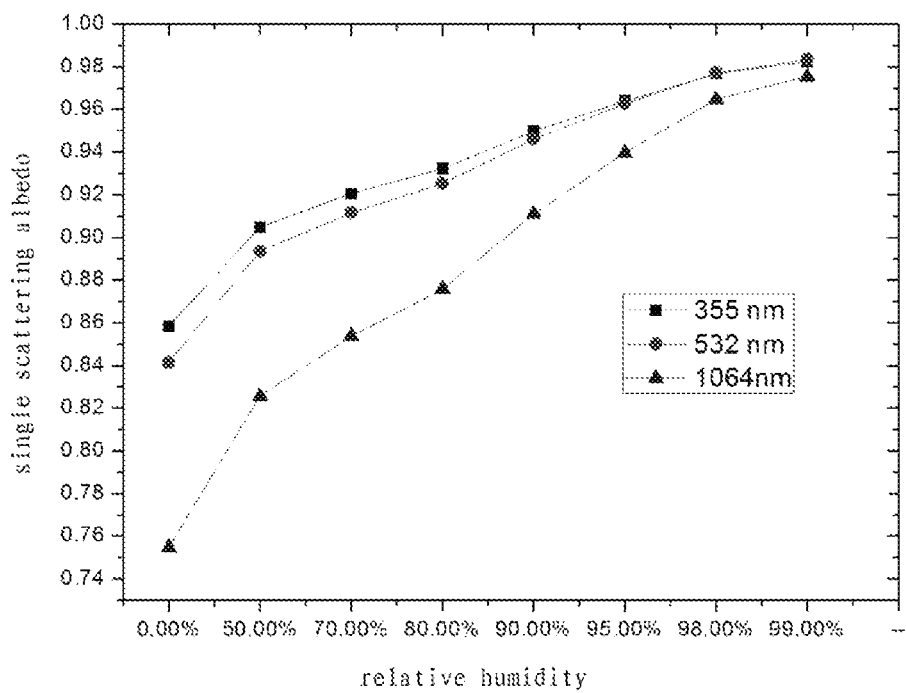
FIG. 7 is a chart of changes in aerosol single scattering albedo along with relative humidity on three channels of 355 nm, 532 nm and 1064 nm wavelengths of the multi-channel aerosol scattering absorption measuring instrument of the present invention.

FIG. 7 is a diagram of changes in aerosol single scattering albedo along with relative humidity on three channels of 355 nm, 532 nm and 1064 nm wavelengths. Single scattering albedo refers to the proportion of reactive scattering part to entire extinction, and shows different with different wavelengths, different relative humilities and different particle radii.

6. Scattering Phase Function

If the measured values distributed at different scattering angles is $\sigma_{sca}(\lambda,\theta_i)$ (in which $\lambda$ is 355 nm, 532 nm and 1064 nm; and scattering angle $\theta_i$ is 3° and 177°, 33° and 147°, 55° and 125°, 90°, and 1 to 179°), and the scatter value $\sigma_{simulated}(\lambda,\theta_i)$ of each scattering angle is calculated according to Lorenz-Mie and T-matrix theories, the difference therebetween is represented as follows:

$$e(\lambda,\theta_i) = \sigma_{sca}(\lambda,\theta_i) - \sigma_{simulated}(\lambda,\theta_i) \quad (8)$$

If $\Sigma[e(\lambda,\theta_i)]^2$ is minimal, the deviation ratio $k(\lambda,\theta)$ between measured value and simulated value in this case is calculated, then the phase function curve is corrected, as a result, the scattering phase function is obtained. During the calculation of scattering phase function of aerosol particles, it should be considered that the scattering phase function of gas molecules needs to be subtracted.

7. Transmittance

Transmittance can be represented by the following equation:

$$T(\lambda) = \frac{I_{(out)}(\lambda)}{I_{(in)}(\lambda)} \cdot \xi_{calibration}(\lambda) \cdot F(\lambda) \quad (9)$$

In the above equation, $I_{(in)}(\lambda)$ and $I_{(out)}(\lambda)$ represents incident light intensity and emergent light intensity respectively, $\xi_{calibration}(\lambda)$ represents calibration coefficient, $F(\lambda)$ represents transfer function, calculated via the two processes of zero gas calibration and calibration gas calibration. During the calculation of transmittance, the influence of transfer function of the cavity should be considered, and the measurement of aerosol transmittance can be achieved by calibration.

The instrument of the invention can not only directly measure the scattering phase function and absorption coefficient of aerosols but also achieve multi-channel (three wavelengths), multi-angular (3° and 177°, 33° and 147°, 55° and 125°, 90°, 1° to 179°), full-scale (0.001-100 μm) photoacoustic/spectral in synchronous on-line direct measurement of aerosol scattering phase function and absorption coefficient, which fully cover the whole scattering spatial/intensity distribution of aerosol particles and accurately acquiring aerosol scattering coefficient, extinction coefficient, transmittance, visibility, single scattering albedo on the basis of precise acquisition of aerosol scattering phase function and absorption coefficient, thereby achieving in synchronous integrated acquisition of all optical characteristics of aerosols.

The invention claimed is:

1. A multi-channel aerosol scattering absorption measuring instrument, comprising a light path device, a detection device and a gas path device, wherein said light path device is used for supplying a light source, said detection device comprises a control unit and a detection unit, said detection unit comprises a photoacoustic cavity, a first long-range multiple reflector, a second long-range multiple reflector, 4-10 photoelectric detectors, a temperature/pressure/humidity sensor and a sound converter, wherein the first long-range multiple reflector and second long-range multiple reflector are positioned at the two ends of the photoacoustic cavity respectively, wherein one photoelectric detector is arranged outside the detection device for measuring light intensity of the light source from the detection unit and other photoelectric detectors are arranged on the inner surface of the photoacoustic cavity for measuring the scattering intensities of an aerosol at different angles, said temperature/pressure/humidity sensor and sound converter are arranged on the inner surface of the photoacoustic cavity, wherein the sound converter is arranged in the middle position of the photoacoustic cavity and perpendicular to the long axis of the photoacoustic cavity, said photoelectric detectors, temperature/pressure/humidity sensor and sound converter are connected to said control unit respectively, said gas path device comprises a sample loading unit, a calibration unit and a sample discharging unit, wherein said sample loading unit and sample discharging unit communicate with the two ends of said photoacoustic cavity respectively, the light source from the light path device and a gas flow from the gas path device enter the photoacoustic cavity of the detection device and are detected by the control unit respectively, and wherein the number of the photoelectric detectors positioned on the surface of the photoacoustic cavity is five, being a first photoelectric detector, a second photoelectric detector, a third photoelectric detector, a fourth photoelectric detector and a fifth photoelectric detector, respectively, wherein the detection angle of the first photoelectric detector ranges from 3° to 177°, the detection angle of the second photoelectric detector ranges from 33° to 147°, the detection angle of the third photoelectric detector ranges from 1° to 179°, the detection angle of the fifth photoelectric detector ranges from 55° to 125°, and the five photoelectric detectors are mounted on the inner surface of the photoacoustic cavity in terms of the detection angles.

2. The multi-channel aerosol scattering absorption measuring instrument according to claim 1, wherein said light path device comprises a laser transmission unit and a laser modulation unit, which are connected in sequence, said laser transmission unit comprises a laser and a controller of the laser, said laser transmission unit transmits a laser beam of 1064 nm fundamental wavelength, said laser modulation unit comprises a frequency multiplication unit, a frequency division unit and a light coupling unit, which are connected in sequence, and said laser modulation unit modulates the fundamental laser beam of 1064 nm into laser beams of 1064 nm, 532 nm and 355 nm wavelengths, respectively.

3. The multi-channel aerosol scattering absorption measuring instrument according to claim 2, wherein said frequency multiplication unit comprises a chopper, a first lens, a first LBO frequency-tripling crystal, a second lens and a second LBO frequency-tripling crystal, wherein the laser beam of 1064 nm wavelength from the laser transmission unit is frequency-modulated by the chopper and then goes through the first lens and first LBO frequency-tripling crystal in sequence, resulting in laser beams of 1064 nm and 532 nm wavelengths, and said laser beams of 1064 nm and 532 nm go through the second lens and second LBO frequency-tripling crystal in sequence, resulting in laser beams of 1064 nm, 532 nm and 355 nm wavelengths.

4. The multi-channel aerosol scattering absorption measuring instrument according to claim 2, wherein said frequency division unit comprises a third lens, a fourth lens, a fifth lens, a first beam splitter, a second beam splitter, a first light chopper, a second light chopper and a third light chopper, the laser beam from the frequency multiplication unit goes through the third lens and first beam splitter in sequence so that the laser beam is divided into a first light beam and a second light beam, wherein the first light beam goes through the first light chopper to form a laser beam of 355 nm wavelength, the second light beam goes through the fourth lens and second beam splitter in sequence so that the laser beam is divided into a third light beam and a fourth light beam, wherein said third light beam goes through the second light chopper to form a laser beam of 532 nm wavelength, and the fourth light beam goes through the fifth lens and the third light chopper to form a laser beam of 1064 nm wavelength.

5. The multi-channel aerosol scattering absorption measuring instrument according to claim 2, wherein said light coupling unit comprises a sixth lens, a seventh lens, an eighth lens, a ninth lens, a tenth lens, an eleventh lens, a twelfth lens, a thirteenth lens, a first folding mirror, a second folding mirror, a third folding mirror, a light coupler and a light collimator, wherein the laser beam of 355 nm wavelength from the light path device goes through the sixth lens, first folding mirror and seventh lens in sequence and then enters the light coupler, the laser beam of 532 nm wavelength from the light path device goes through the eighth lens, second folding mirror and ninth lens in sequence and then enters the light coupler, the laser beam of 1064 nm wavelength from the light path device goes through the tenth lens, third folding mirror and eleventh lens in sequence and then enters the light coupler, and the three laser beams of different wavelengths enter the light coupler in sequence, then enter the light collimator after going through the twelfth lens in sequence and finally enter the detection device after going through the thirteenth lens.

6. The multi-channel aerosol scattering absorption measuring instrument according to claim 1, wherein said sample loading unit comprises an aerosol cutting head, a flow meter, three-way valves and a mass flow meter, which are connected in sequence, and said aerosol sampling gas flow firstly goes through the aerosol cutting head and flow meter and then enters the detection device after going through the three-way valves and mass flow meter, wherein a temperature/pressure/humidity sensor is arranged between said three-way valves and said mass flow meter.

7. The multi-channel aerosol scattering absorption measuring instrument according to claim 1, wherein said calibration unit comprises a zero gas generator, a first calibration gas source and a second calibration gas source, wherein a zero gas from the zero gas generator, a first calibration gas from the first calibration gas source and a second calibration gas from the second calibration gas source go through the mass flow meter respectively and then enter the detection unit.

8. The multi-channel aerosol scattering absorption measuring instrument according to claim 1, wherein said sample discharging unit comprises a mass flow meter, a flow meter and a pump, which are connected in sequence, and the gas flow going through the detection unit goes through the mass flow meter and flow meter in sequence and then is discharged from the detection unit under the pulling action of the pump, wherein a temperature/pressure/humidity sensor is arranged between said mass flow meter and said flow meter.

9. The multi-channel aerosol scattering absorption measuring instrument according to claim 1, wherein said multi-channel aerosol scattering absorption measuring instrument is provided with a temperature control unit, said temperature control unit comprises a double-layer stainless steel case body, semiconductor refrigerators, heat-exchange fans and a temperature/pressure/humidity sensor, wherein said double-layer stainless steel case body is mounted outside said detection device, said semiconductor refrigerators, heat-exchange fans and temperature/pressure/humidity sensor are arranged on the surface of the double-layer stainless steel case body respectively, a window is formed on one side of said double-layer stainless steel case body so that a light source from the light path device enters said detection device, the data of said temperature/pressure/humidity sensor is transmitted to the control device, and according to the transmitted data, the control device determines whether to start the semiconductor refrigerators and heat-exchange fans to control the temperature in the double-layer stainless steel case body.

10. The multi-channel aerosol scattering absorption measuring instrument according to claim 1, wherein said multi-channel aerosol scattering absorption measuring instrument is provided with an inlet gas sound insulation device and an exhaust gas sound insulation device, wherein said inlet gas sound insulation device comprises a first buffer, a first sound filter and a second buffer, which are connected in sequence, wherein said first buffer is mounted to the exit of the sample loading unit and connected to a first receiver, and said second buffer constitutes one end of said photoacoustic cavity, and said exhaust gas sound insulation device comprises a third buffer, a second sound filter and a fourth buffer, wherein said third buffer is mounted to the entrance of the sample discharging unit and connected to a second receiver, and said fourth buffer constitutes the other end of said photoacoustic cavity.

* * * * *